United States Patent [19]

Gazielly et al.

[11] Patent Number: 5,195,542
[45] Date of Patent: Mar. 23, 1993

[54] REINFORCEMENT AND SUPPORTING DEVICE FOR THE ROTATOR CUFF OF A SHOULDER JOINT OF A PERSON

[76] Inventors: Dominique Gazielly, 47 Rue Henri Déchaud, 42100 Saint Etienne; Pierre Blondel, La Forie, 63600 Ambert, both of France

[21] Appl. No.: 623,641

[22] PCT Filed: Apr. 25, 1990

[86] PCT No.: PCT/FR90/00291
§ 371 Date: Dec. 13, 1990
§ 102(e) Date: Dec. 13, 1990

[87] PCT Pub. No.: WO90/12551
PCT Pub. Date: Nov. 1, 1990

[30] Foreign Application Priority Data

Apr. 27, 1989 [FR] France ................... 89 06005

[51] Int. Cl.⁵ .......................... A61B 19/00; A61F 2/40
[52] U.S. Cl. ..................................... 128/898; 602/44; 606/151; 623/19
[58] Field of Search ................ 606/151; 128/155, 898; 623/1, 18, 19, 13; 602/44

[56] References Cited

U.S. PATENT DOCUMENTS

| | | | |
|---|---|---|---|
| 3,029,819 | 4/1962 | Starks | 623/1 |
| 3,570,013 | 3/1971 | Blumen | 623/1 |
| 3,945,052 | 3/1976 | Liebig | 623/1 |
| 4,347,847 | 9/1982 | Usher | 128/334 |
| 4,502,161 | 3/1985 | Wall | 623/18 |
| 4,759,765 | 7/1988 | Van Kampen | 623/13 |
| 4,769,038 | 9/1988 | Bendavid et al. | 623/13 |
| 4,795,466 | 1/1989 | Stuhmer et al. | 623/13 |
| 4,932,972 | 1/1990 | Dunn et al. | 623/13 |

FOREIGN PATENT DOCUMENTS

| | | |
|---|---|---|
| 0169045 | 1/1986 | European Pat. Off. . |
| 0239775 | 10/1987 | European Pat. Off. . |
| 3008270 | 9/1981 | Fed. Rep. of Germany . |
| WO/9103993 | 4/1991 | PCT Int'l Appl. ........ 623/19 |

*Primary Examiner*—Stephen C. Pellegrino
*Assistant Examiner*—Gary Jackson
*Attorney, Agent, or Firm*—Parkhurst, Wendel & Rossi

[57] ABSTRACT

The present invention relates to a rotator cuff reinforcement device for surgical implantation to a shoulder of a person, including a strip having a rear heel for fixation to at least one of a trochiter and a tendinous mass of a rotator cuff, the strip having a linear extension or divergent legs from the heel defining opposite end(s) for fixation to respective tendon(s) of such a rotator cuff.

2 Claims, 3 Drawing Sheets

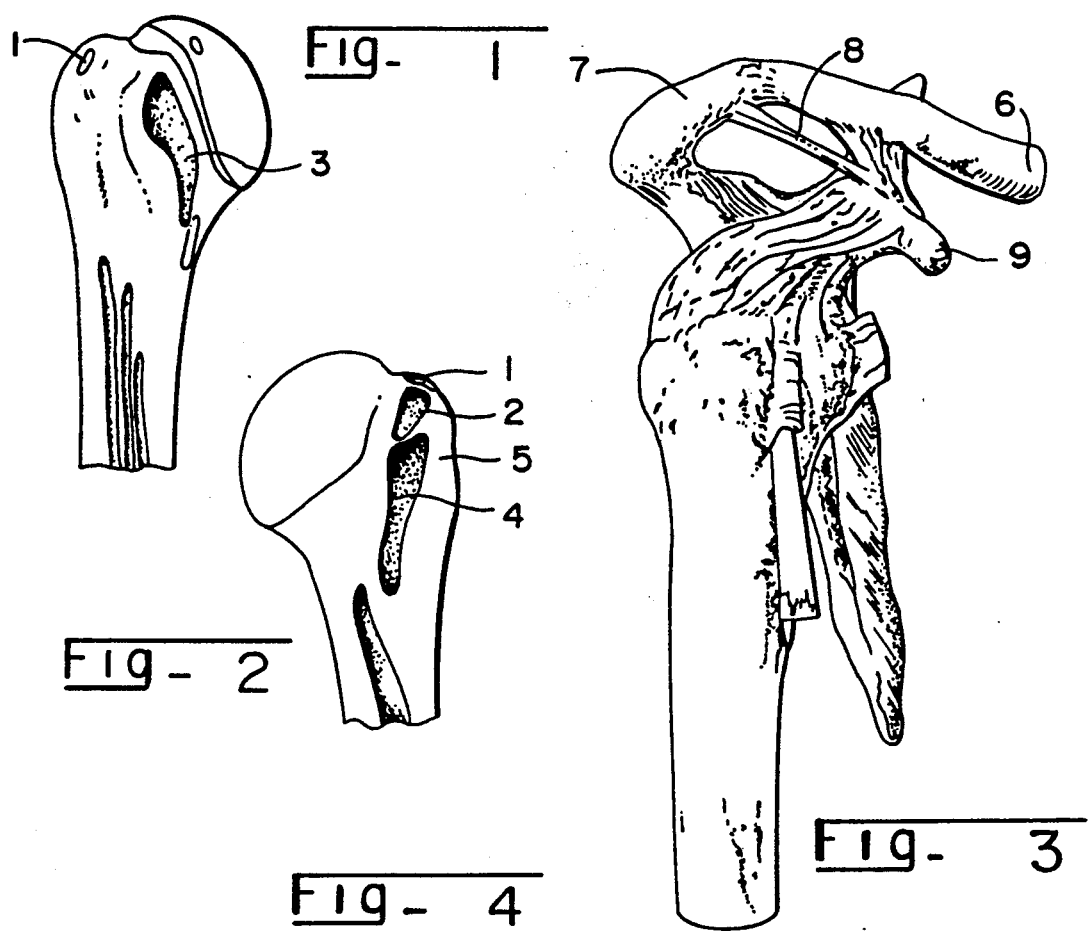
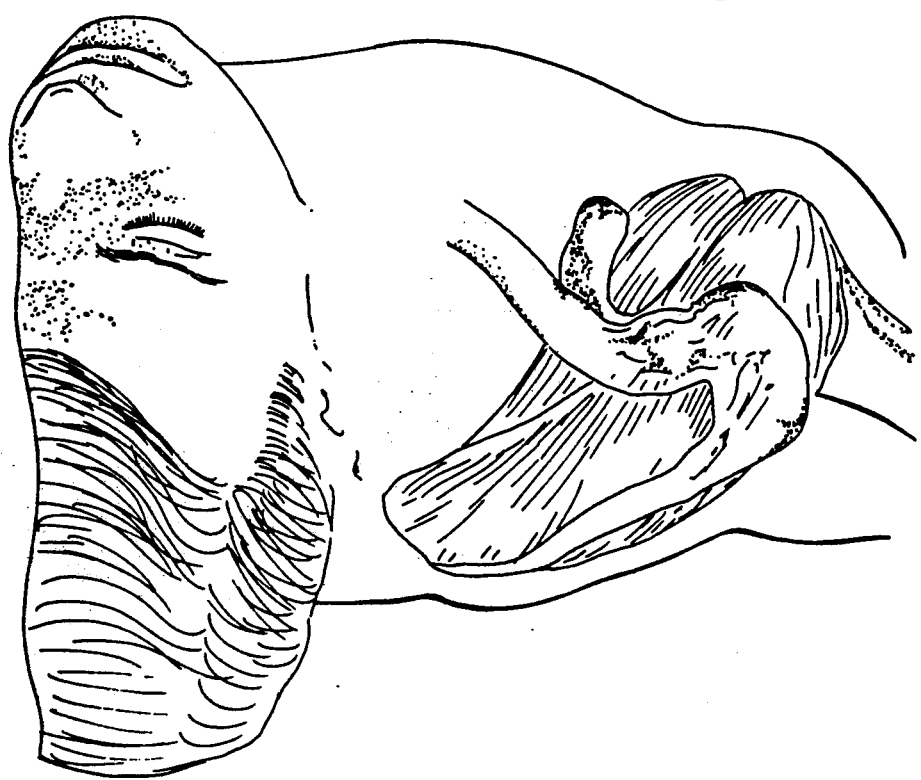

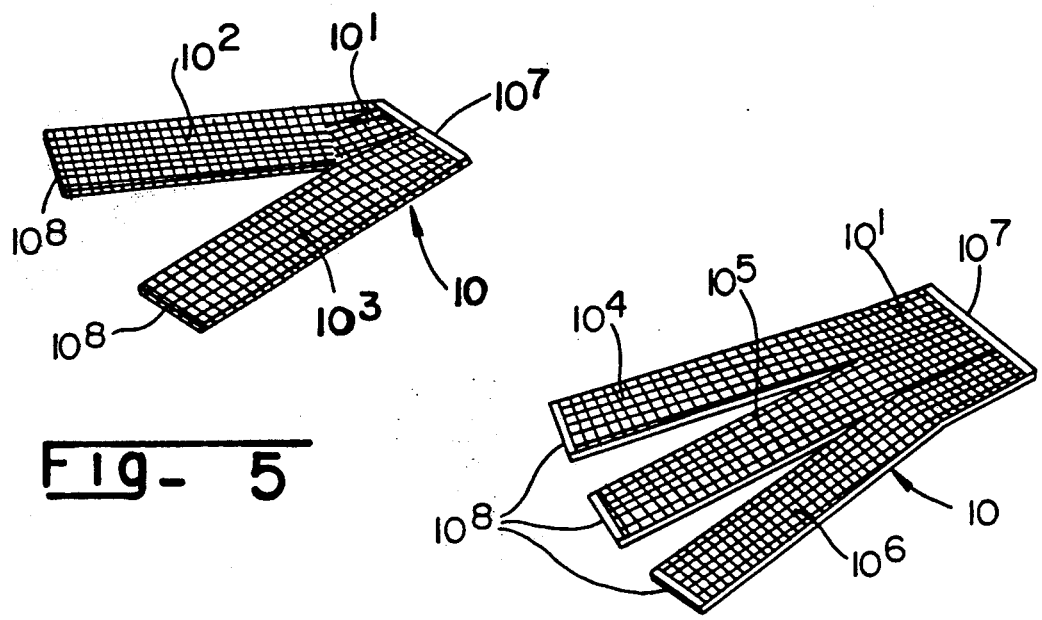
Fig. 5
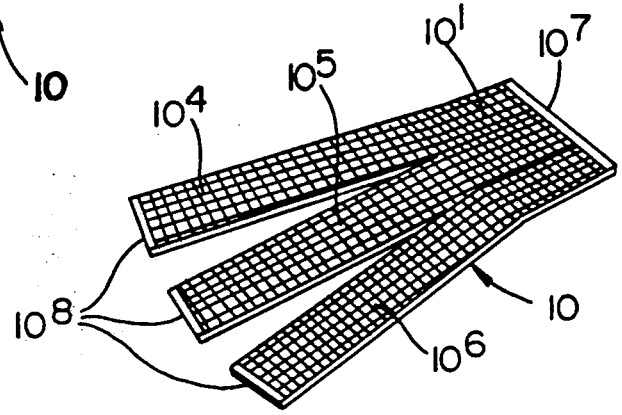
Fig. 6
Fig. 7
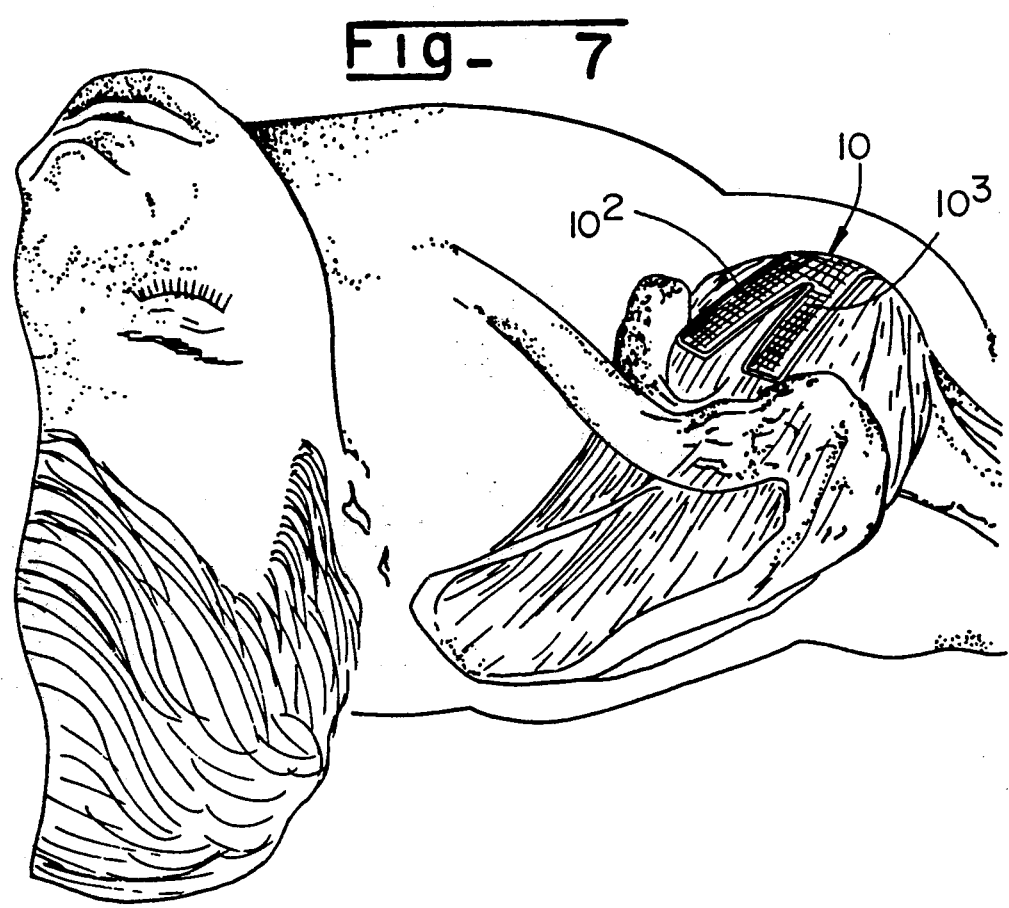

REINFORCEMENT AND SUPPORTING DEVICE FOR THE ROTATOR CUFF OF A SHOULDER JOINT OF A PERSON

BACKGROUND OF THE INVENTION

The present invention relates to the technical sector of surgery of the shoulder and means to provide therapy in particular. In order to understand the objects and advantages of the invention, its environment with regard to degenerative ruptures of rotator cuffs will be briefly discussed.

FIELD OF THE INVENTION The rotator cuff of a shoulder joint is made up by the distal tendinous portion of four muscles, supraspinatus and subspinatus (1) (2), subscapularis (3) and teres minor (4), (FIGS. 1 and 2). The cuff is attached to the upper, anterior and posterior faces of the trochiter (5) by covering the upper pole of the humeral head. The function of this tendinous cuff, 3 to 4 millimeters thick, depends on the fundamental centering and stabilizing role of the numeral head with respect to sliding action during anterior and lateral lifting and rotation movements of the arm.

The musculotendinous cuff passes under an osteofibrous arch, which is made up from the front to the rear by a portion of the acromion (7), the coracoacromial ligament (8) and the coracoid process (9), (FIG. 3), thereby forming a canal. (6) represents a partial section of the clavicle. A sliding bursa passes is inerted between the musculotendinous cuff and the walls of the osteofibrous arch. Therefore, there is a potential and sometimes detrimental interaction between the musculotendinous cuff and the acromiocoracoidan arch, particularly during lateral and anterior lifting movements of the arm. The repeated rubbing of the cuff against the walls of the osteofibrous arch results in wearing of the tendinous cuff by progressive abrasion. The rubbing can be increased in as much as arthosis lesions with severe osteophytes may thickens the walls of the aforementioned such becoming more aggressive as the cuff gets older. With time, gradual thinning is brought about and a trophic perforation (less than 1 cm$^2$) of the cuff, particularly in the hypo-vascularized and fragile area where the supraspinatus muscle passes, may occur. A fall may provide a more extensive rupture by retraction of the supraspinatus muscle, with extension towards the front (subscapularis muscle) or the rear (subepinatus muscle). The degenerative rupture of the rotator or musculotendinous cuff may be of a varied size:

—grade 1—perforation (less than 1 cm$^2$) reaching the supraspinatus muscle

—grade 2—supraspinatus rupture (greater than 1 cm$^2$)

—grade 2—Massive rupture concerning the supraspinatus, subspinatus, subscaptularis muscles and sometimes the teres minor muscle.

It is possible to carry out surgery to reconstruct the rotator cuff. This is done by recovering the numeral head, giving back the cuff its capturing and stabilizing role and reestablishing establishing a harmonious scapulohumeral rhythem. Reconstruction requires excision of the coracoacromial ligament and cleaning the subacromial space, including suppression of the arthrosis legions and thinning of the anterior portion of the acromion.

Several processes are therefore possible in order to cover the numeral head.

DESCRIPTION OF SURGICAL PROCESSES

Certain processes do not use the rotator cuff, such as when the tendinous cuff has disappeared due to wear or major retraction. It is technically possible to fill in the space corresponding to the cuff by covering the humeral head with a natural or synthetic, inert material. However, it appears preferable, in the case of major ruptures, where the numeral head is uncovered, to carry out plasty by the anterior deltoid muscular flap, which offers the advantage of covering the humeral head and having a lowering effect of the humeral head by active contraction of the flap.

Other surgical processes use the rotator cuff. The rotator cuff is disinserted. The humeral head is uncovered when there is a more or less significant lack of covering (grades 1, 2, 3). The tendons are retracted according to a variable degree, however it is possible to free the adherences in order to bring them to their initial trochiterian insertion area. Just like a mobile roof, the cuff, retracted towards the scapula, covers the humeral head again. Therefore, only the tendons need to be attached to the trochiter by sutures using non-reabsorbable thread, made at the bottom of a bone trench. The reconstruction must be isometrically enabling, which may be done by visually examining during operation, the internal and external rotation movements and with the elbow against the body, and bending and extension movements, to ensure that the transosseous reinsertion sutures hold.

If the extent of the loss of tendinous substance and/or the degree of retraction, prevent solid and reliable reinsertion authorizing immediate and post-operative rehabilitation, it is preferable to use a deltoidian flap rather than to try to fill in the space left free by a cuff, remaining after random reinsertion, by a synthetic or other type of material. In the case of average retraction, which does not allow for direct reinsertion of the supraspinatus muscle tendon, some authors recommend rotation flaps of the subscapularis muscle and/or the subspinatus muscle.

SUMMARY OF THE INVENTION

According to the above explanations, it can be understood that surgery of the shoulder is delicate, complex and a maximum of precautions have to be taken in order to guarantee the operation reliable. It is also necessary to take into account the fact that the tissues are worn, thin and old. It is for this reason that a first aim according to the present invention was to look into reinforcing the tendons reinserted which are thin or fragile, including by infiltrations of corticoids, and thus provide surgical therapy for the rupture or weakening of the rotator cuff of a shoulder joint of a person.

Another aim according to the invention was to produce a simple device, easily manufactured and biologically compatible within the human body.

Another aim according to the invention was to provide mechanical reinforcement by adding a substance enabling the tendinous reinsertion zone to be protected and authorizing more active post-operative rehabilitation.

Another aim according to the invention was to obtain thickening of the tendons, enabling a final biological reinforcing effect by integration of the material initially added.

These aims and others shall be made well apparent from the following description.

According to a first characteristics, the device used for aiding in surgical therapy of the rupture or weakening of the rotator cuff of a shoulder joint of a person, is characterized by a strip with a rear heel fixed onto the trochiter or the tendinous mass of the cuff and extending, in a linear manner, or by at least two divergent legs, towards the top of the cuff and having end(s) thereof being fixed onto the tendon(s).

According to another characteristic, the device is characterized wherein the strip is extended by at least two divergent legs wherein one of the legs is fixed to the repaired tendon in order to reinforce it and protect it and the other leg(s) are fixed onto the other healthy tendon(s) according to the biomechanical working axes of the shoulder rotator cuff tendons.

According to another characteristic, the device is characterised wherein the strip is made of a thin, sterile biocompatible material.

BRIEF DESCRIPTION OF THE DRAWINGS In order to clarify the invention, in a non-limiting manner the invention is illustrated by the accompanying drawings wherein :

FIGS. 1 and 2 are partial views of the anterior and posterior face of the top end of the right humerus of the person.

FIG. 3 is an external side view of the joints of the right shoulder.

FIG. 4 is a top view showing the rotator cuff.

FIG. 5 is a view of a tendon holding and supporting device according to the present invention comprising a heel extended by two legs.

FIG. 6 is a view of the device as an alternative model comprising a heel and three legs.

FIG. 7 is a view illustrating the application of the device according to the invention in order to support certain tendons.

Figure 8:
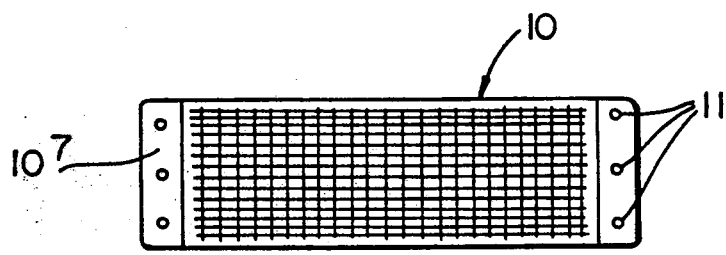
FIG. 8 shows the device seen in a plan view, in a simple geometrical form.
Figure 9:
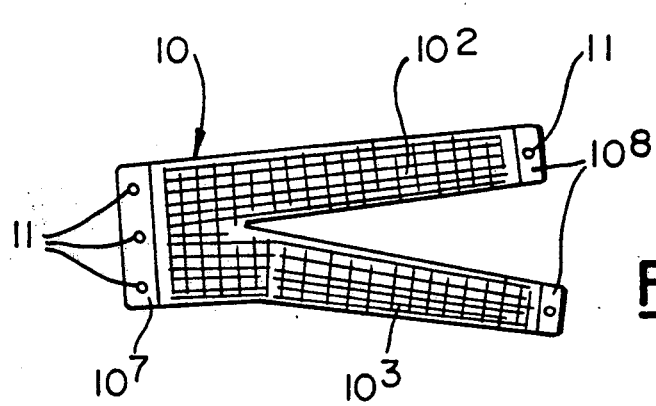
FIGS. 9 and 10 are views showing the device of FIGS. 5 and 6 provided with fixing means at its ends.
Figure 10:
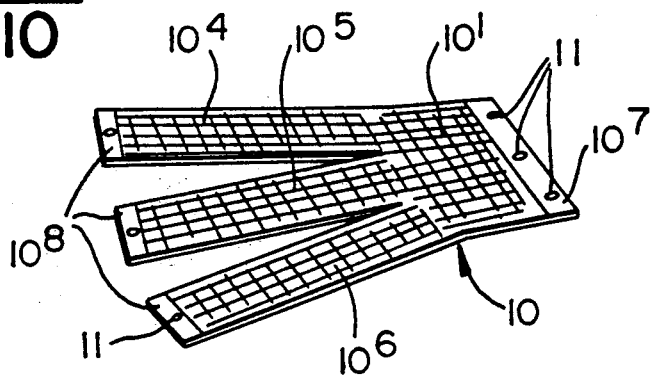

The object of the invention will become more apparent from the following non-limiting detailed description, when considered in conjunction with the drawings.

DETAILED DESCRIPTION OF THE PREFERRED EMBODIMENTS

The device according to the present invention is used in surgical therapy of the rupture or weakening of the rotator cuff of a shoulder joint.

The device is in the form of a strip (10) of a simple, rectangular or trapezoidal geometrical shape, or complex with two or several legs (10.2, 10.3, 10.4 10.5 10.6). The device is produced in the form of a strip by, for example, of being braided, knitted, woven, and more generally, made of all biocompatible materials. This strip is thin, sterile, biocompatible and short. The strap has, firstly, a base or heel (10.1) fixed by its ends (10.7) on the trochiterian support or the tendinous mass of the cuff, and, secondly, is extended in a linear manner, or by two or three legs diverging towards the top of the cuff according to the biomechanical working axes of the rotator cuff tendons.

The strip is extended towards the front by at least two divergent legs (10.2-10.3) defining a Y shape, for application and fixing to tendons (FIG. 5). In an alternative form, according to FIG. 6, the strip has three diverging legs (10.4, 10.5, 10.6) in a ψ shape. The general aspect of the strip as such, is rectangular or trapezoidal shaped and enables the reinforced cuff to work according to the biomechanical lines of forces, in the direction of the different tendons. According to a specific positioning, one of the legs (10.2-10.3) or (10.4, 10.5, 10.6) of the strip, is fixed and sewn by the end (10.8) onto the repaired tendon, thinned down and thus reinforced thereby protecting it, whereas the other leg(s) of the strip are sewn to the ends (10.8) on the other healthy tendon(s). The shape of the strip with three legs thereby enables sewing onto the supraspinatus, subspinatus and subscapularis tendons.

The legs (10.2, 10.3, 10.4, 10.5, 10.6) can be the same length or different lengths.

In its inner shape, the strip provides support of the tendon during weakening before rupture.

According to another arrangement, the ends (10.7 and 10.8) of the strip, are made of a semi-rigid or flexible mass resulting from melting the component threads. They may include holes (11) made in this mass, facilitating the binding of the device on the trochiter or tendinous mass and on the healthy tendon(s). These holes exist in a number adapted to provide the binding and fixing.

Therefore, the shape with the holding and supporting device according to the invention, enables it to match the tendons of the rotator cuff perfectly thereby taking up the minimum of space so as not to cause an iatrogenic subacromial anterior conflict by increasing the bulk of the rotator cuff.

Furthermore, the device must be positioned on a reconstructed cuff, in an isometric manner, in order to enable the tendons to operate in the direction of the fibres and without excessive pulling.

According to another arrangement of the invention, the holding and supporting strip is made of a biologically compatible material, thus enabling it to be biologically integrated into living tissues. In an advantageous manner, this a braided polypropylene material. The material selected, enables gradual integration of the reinforcing and holding strip thereby providing thickening of the reconstructed cuff and therefore, biological reinforcement.

The advantages are clearly set forth in the present specification. In particular, the simplicity of the design of the reinforcing and holding strip, its easy adaptation to a reconstructed inserted cuff, are highlighted.

We claim:
1. A method of reinforcing a rotator cuff of a person, comprising the steps of:
   fixing a rear heel of a strip to at least one of a tendinous mass and a trochiter of such a rotator cuff, said rear heel having a linear extension defining an opposite end; and
   fixing said opposite end to a tendon of such a rotator cuff.
2. A method of reinforcing a rotator cuff of a person, comprising the steps of:
   fixing a rear heel of a strip to at least one of a tendinous mass and a trochiter of such a rotator cuff, said rear heel having at least two divergent legs defining at least two respective divergent ends; and
   fixing said at least two divergent ends to tendons of said rotation cuff.

* * * * *

UNITED STATES PATENT AND TRADEMARK OFFICE
CERTIFICATE OF CORRECTION

PATENT NO. : 5,195,542
DATED : March 23, 1993
INVENTOR(S) : Dominique Gazielly and Pierre Blondel It is certified that error appears in the above-identified patent and that said Letters Patent is hereby corrected as shown below:

Col. 4,
Claim 1, line 3, delete "at least one of a tendi-"; and
       line 4, delete "nous mass and".

Col. 4,
Claim 2, line 3, delete "at least one of a tendi-"; and
       line 4, delete "nous mass and".

Please add claims 3 and 4 as follows:

3. The method of claim 1, wherein the rear heel of the strip is inserted into a trench or groove formed in the trochiter and sutured therein.

4. The method of claim 2, wherein the rear heel of the strip is inserted into a trench or groove formed in the trochiter and sutured therein.

Signed and Sealed this

Twenty-sixth Day of April, 1994

Attest:

BRUCE LEHMAN

Attesting Officer     Commissioner of Patents and Trademarks